(12) United States Patent
Gokhfeld

(10) Patent No.: US 7,062,952 B2
(45) Date of Patent: Jun. 20, 2006

(54) COMBUSTIBLE GAS DETECTOR HAVING FLOW-THROUGH SENSOR CONTAINER AND METHOD FOR MEASURING SUCH GASES

(75) Inventor: Yuzef Gokhfeld, Waltham, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/442,070

(22) Filed: May 21, 2003

(65) Prior Publication Data

US 2004/0231399 A1    Nov. 25, 2004

(51) Int. Cl.
*G01N 7/00* (2006.01)
(52) U.S. Cl. .................................... 73/23.31
(58) Field of Classification Search ............... 73/23.31; 702/30
See application file for complete search history.

(56) References Cited

U.S. PATENT DOCUMENTS

| 2,349,250 A | * | 5/1944 | Doan ......................... 324/71.1 |
| 2,663,379 A | | 12/1953 | Lloyd |
| 3,375,700 A | | 4/1968 | Hubner |
| 3,687,631 A | | 8/1972 | Zegel |
| 4,115,229 A | | 9/1978 | Capone et al. |
| 4,169,769 A | | 10/1979 | Capone |
| 5,748,492 A | * | 5/1998 | Vander Heyden et al. .... 702/30 |

FOREIGN PATENT DOCUMENTS

| GB | 520 993 | 5/1940 |
| GB | 2 044 462 | 10/1980 |
| GB | 2 329 716 | 3/1999 |
| RU | 2 142 624 | 12/1999 |
| RU | 2 156 972 | 9/2000 |
| SU | 1170277 | 7/1985 |
| WO | 03/008928 | 1/2003 |

\* cited by examiner

*Primary Examiner*—Hezron Williams
*Assistant Examiner*—John Fitzgerald
(74) *Attorney, Agent, or Firm*—Nixon & Vanderhye P.C.

(57) ABSTRACT

An apparatus and method to measure combustible gases using a catalytic sensor includes: housing the catalytic sensor in a flow-through chamber isolated from a volume of ambient gas; periodically drawing into the chamber a sample of the ambient gas; burning on the catalytic sensor and in the chamber the combustible gas in the sample of ambient gas, e.g. essentially until the completion of burn out, and measuring the plurality of output signals of the sensor synchronously with the interrupted ambient gas sampling while burning the sample on the catalytic sensor.

16 Claims, 6 Drawing Sheets

COMBUSTIBLE GAS DETECTOR HAVING FLOW-THROUGH SENSOR CONTAINER AND METHOD FOR MEASURING SUCH GASES

BACKGROUND OF THE INVENTION

There are several known methods to detect the presence and measure the concentration of combustible gases and vapors (collectively referred to herein as "combustible gases" or "combustibles"). In one such method, the combustible gases are detected based on the actually measuring the rate of heat liberation during catalytic combustion. A combustible gas detector detects and measures combustible gases by burning a gas sample on a catalytic sensor. Catalytic combustion occurs in the sensor on a surface of a heated porous substrate, e.g. silica or alumina that has been impregnated with a catalyst. The resulting increase in temperature of the substrate is proportional to the rate of heat generation during the catalytic combustion and is measured electronically by sensing a resistance change of an imbedded resistance temperature detector (RTD).

A known type of catalytic combustible gas detector has a catalytic bead sensor, a reference bead, and a Wheatstone bridge. The bead sensor conventionally includes a catalyst-impregnated substrate in a form of a small bead, an RTD and a heater combination made as a tiny Platinum (Pt) wire coil imbedded in the body of the bead. Typically, the reference bead (also referred to as a compensating bead) is similar to the catalyst-impregnated bead with a heater, except that the compensating bead is not impregnated with a catalyst. The sensing and reference beads are supported by the Pt wires, which are the extensions of the heating coils. The catalyst impregnated bead and reference bead may be shielded from ambient gas by a porous cup (enclosure). The cup enclosure is permeable to the gas so as to allow ambient gas to reach the beads, essentially by means of diffusion. The cup may be formed out of stainless steel gauze or a more robust porous material, e.g. sintered ceramic. A porous ceramic cup may also serve as a flame-retarding barrier to explosion proof the detector design.

Conventional catalytic sensors are exposed to a continual influx of combustible gas that diffuses toward the beads from the environment. The sample gas may also reach the beads by convection. Gas velocity variations around the sensor in this case may provoke false sensor readings. Prior attempts to reduce measurement error due to gas velocity variations tend to diminish the sensor sensitivity and prolong the response time of the sensor.

Catalytic sensing beads and reference beads of conventional sensors are typically connected as the resistive shoulders of a balanced Wheatstone bridge circuit. Combustion heating on the sensing bead causes the resistance of the RTD imbedded into sensing bead change with respect to the resistance of the reference bead RTD to create a bridge misbalance.

The output voltage of the bridge is indicative of the resistive misbalance between the sensing and reference RTDs and is output as a signal from which concentration of combustible gas(es) is derived. However, the bridge misbalance in a conventional detector may be influenced by factors other than the catalytic combustion on the sensing bead, including: aging of the beads, changes in the background such as variations in ambient temperature, non-combustible gas mixture composition, and radiation absorption in the vicinity of the sensor beads due to different moisture concentrations. These other factors may significantly raise the lower detection limit of the detector, and cause the response of the detector to drift out of its rated detection level or range for combustible gases.

The sensitivity to combustible gases of a conventional catalytic detector may also be reduced due to "poisoning" of the catalyst in the sensor bead. When poisoned, sensors become less sensitive to combustibles. Reduced sensitivity to combustible gases and sensor drift are troublesome for a catalytic detector, especially for those used in critical applications, such as lower explosive limit (LEL) detectors that are employed to prevent fire and explosions.

"Poisoning" of catalytic bead sensors is conventionally detected by direct application of a gas sample with a known concentration of combustibles. With diffusion type sensors, this procedure is relatively cumbersome. Moreover, long periods of time, e.g. up to several months, may pass between when the detector looses sensitivity and when the sensitivity loss in the detector is discovered. A poisoned detector may fail to detect a dangerous level of combustibles. Implementation of automated or frequent manual sensitivity check-up in a conventional detector is usually cost-prohibitive.

Conventional catalytic bead sensors can be made more or less selectively sensitive to some groups of gases, which is generally achieved by choosing a specific temperature setting of the catalytic bead. This temperature selection technique may not be effective at discriminating between different compositions with two or more combustible gases while using a single sensor and at one fixed temperature. In particular, catalytic bead sensors are practically unable to discriminate between carbon monoxide (CO) and hydrogen ($H_2$) gases. Usually CO and $H_2$ both start catalytically burning at nearly the same "low" catalyst temperature and are practically indistinguishable based on the temperature set-up of the bead(s). Accordingly, conventional catalytic detectors tend to be ineffective at: measuring low combustible gases concentrations, e.g., concentrations below 500 ppm (parts per million) over an extended time period, maintaining a stable "zero" without drifting over a period of years, and distinguishing between combustible gases, e.g. between CO and $H_2$.

BRIEF DESCRIPTION OF THE INVENTION

In a first embodiment, the invention is a method to measure combustible gases using a catalytic sensor comprising: housing the catalytic sensor in a flow-through chamber which essentially prevents gas diffusion to the sensor from the volume of ambient gas; drawing a flow of the ambient gas into the chamber; interrupting the flow of the ambient gas into the chamber after a sample of ambient gas has been drawn into the chamber, and measuring an output of the catalytic sensor synchronously with the interruption of the gas flow.

The first embodiment may further include the steps of drawing a gas sample into the chamber with the sensor, and measuring the variation of the output signal within a measurement cycle that is performed repeatedly. In addition, the first embodiment may include (prior to drawing the sample into the chamber) the steps of: purging the chamber with gas sample previously drawn in through the sensor chamber and "inhaled" into the "breathing" pump chamber; burning residual combustible gases in the pump and/or sensor chamber; measuring a reference output signal from the sensor after essentially completely burning the residual combustible gases; drawing in a new gas sample into the sensor chamber from the room through the pump "inhale"; measuring the sensor output signal(s) while burning the new sample; and determining the concentration of combustible gases through the difference between the output signal(s) measured during the burning of the new sample and the reference output signal.

Moreover, the first embodiment may also include repeating the measurement of the output signal during a period starting after the sample is drawn into the chamber and continuing during the burning of the sample; analyzing the dynamics of the sample burning through multiple sensor output measurements, and determining a concentration of at least one combustible gas of a plurality of combustible gases in the sample.

Even further, the first embodiment may include the steps of: purging the chamber of a first gas sample and thereafter measuring a first output signal of the sensor; purging the chamber with a second gas sample enriched with a predetermined amount of hydrogen; thereafter measuring a second output signal of the sensor; and applying a difference between the first output and the second output to determine sensor sensitivity.

In a second embodiment, the invention is a method to measure combustible gases using a detector with a catalytic sensor comprising: housing the catalytic sensor in a flow-through chamber which isolates the sensor from ambient gas; drawing into the chamber a sample of the ambient gas by convection; interrupting and/or reversing gas flow through the chamber to automatically zero the detector by essentially completely burning the combustible gases in the gas sample applied to the sensor inside the chamber, e.g. on the catalytic sensor bead itself; and measuring at least two output signals of the detector synchronously with the sampling rate change.

In a third embodiment, the invention is a detector of combustibles in an ambient gas mixture comprising: a flow-through chamber impervious to gas having a port coupled to a first diffusion preventing passage with minimized gas diffusion capability, e.g. tubing with limited inside diameter (ID), connectable to a volume of the ambient gas mixture, and a second port coupled to a second diffusion preventing passage; a catalytic type sensor of combustible gases installed inside the chamber; a gas pump pneumatically connected to the chamber through the second passage, a pump controller for interrupting and/or alternating gas flow through the chamber. In a more specific second embodiment, the pump inhales and exhausts the ambient gas samples into and from the pump chamber and through the said sensor chamber. In the second embodiment, the first diffusion preventing passage may be a tube with a length in a range of 10 mm to 5000 mm and an interior diameter in a range of 0.1 mm to 3 mm. In the second embodiment, sensor and reference beads of the catalytic sensor are positioned symmetrically against the convectional gas flow through the chamber.

DETAILED DESCRIPTION OF THE INVENTION

Figure 1:
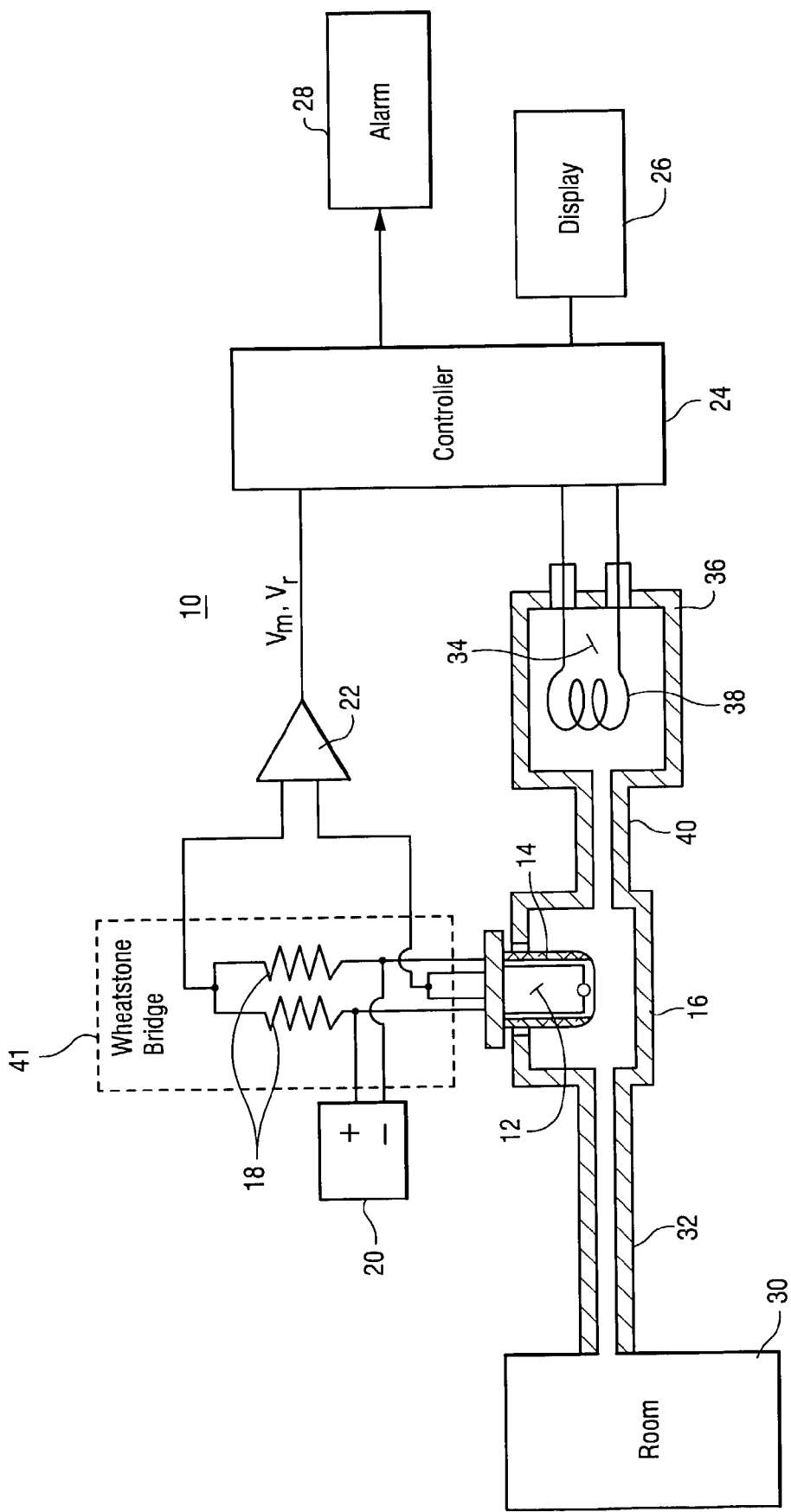
FIG. 1 is a schematic diagram showing in cross-section a first embodiment of a combustible gas detector.

FIG. 1 shows a combustible gas detector 10 having a combustible gas sensor 12 in a porous or other protective enclosure 14 and housed in a flow-through chamber 16. In this design, the protective enclosure 14 is optional and is shown because it is commonly installed by sensor manufacturers in commercially available catalytic sensors. The chamber 16 is impervious to ambient gas diffusion and may be separated from an ambient gas volume 30 by a substantial distance, e.g. up to 10 meters. The chamber has a sample gas inlet pneumatically connected to volume 30 by a diffusion limiting passage 32, and an exhaust passage 40. The passage 32 essentially prevents the diffusion of ambient gas from the volume 30 into the chamber 16 while allowing to drawing in a gas sample by convection. The sensor 12 in the chamber 16 may be a catalytic combustible sensor such as, for example, a conventional catalytic bead sensor having a catalytic sensing bead and a reference bead that are connected as the resistive shoulders 18 of a Wheatstone bridge 41. The bridge 41 is powered by an electrical power supply 20.

The output of the bridge 41 is amplified by a pre-amplifier 22 and then is read by a microprocessor-based controller 24. The controller collects the data from the bridge output for electronic storage and processes the data to analyze whether combustible gases are present in the gas sample or evaluates the concentration and/or composition of the combustible gases based on the bridge 41 output. The controller outputs the results of its data processing to a display device 26, such as a liquid crystal display (LCD), and to a detector interface device 28, such as an alarm device.

The sensor chamber 16 is pneumatically connected to a volume 30 of the ambient gas, such as a room, stack, or other volume potentially having combustible gases. The chamber is isolated from ambient gases so that to preventing them from reaching the sensor 12 by diffusing from the volume 30. The diffusion preventing passage 32 connects the chamber 16 to the gas volume 30. The passage 32 may be a tube having an inside diameter of 0.1 mm to 3 mm and a length of 10 mm to 10,000 mm. More specifically, the dimensions of the passage 32 are chosen to reduce the rate of ambient gas diffusion through the passage to be less than a convection flow rate forced by the sampling pump 34. The passage 32 virtually prevents the diffusion of combustible gases from the outside volume 30. Preventing diffusion gas flow into the chamber 16 facilitates the process of temporary removing the combustibles from the gas sample when the sensor is being zeroed. Passage 32, which minimizes diffusion gas flow, may also serve as a flame arrestor to prevent flashback of flames in the sensor chamber 16. Gas samples flow essentially by convection from the volume 30, through the passage 32 and into the sensor chamber 16. The passage 32 also effectively isolates the chamber 16 from variations in the flow of ambient gas in the volume 30, while providing a conduit for samples of ambient gas to be drawn into the chamber 16.

The volume 30, passage 32, and sensor chamber 16 of the detector are pneumatically connected in series to a gas pump 34. The pump draws a controlled flow of sampled gas from the volume 30, through the passage 32, and into the sensor chamber 16. The pump may be a conventional sampling pump or a "breathing" pump (as shown in FIG. 1) that responds to control signals from the controller 24. The breathing pump 34 may be a sealed pump chamber 36 that houses a heater coil 38 controlled by the controller 24. By heating and cooling the gas in the chamber 36, gas is pumped out of and drawn into the pump chamber 36. A breathing pump is mechanically simple, works reliably, and has longevity. A breathing pump has no moving parts and may operate at ambient temperatures up to about 500° C. Other types of sampling pumps may be employed as well for the pump 34.

The flow of sample into the chamber 16 is interrupted while the sample is burned and measured. Interruption of the sample gas flow can be achieved by controlling the pump 34, or by controlling a by-pass gas flow to the chamber 16, e.g. by employing a solenoid valve connected to the controller. The pump 34 "inhales" a small controlled volume of gas (sample gas), and then purges ("exhale") the sample in a repeating cycle.

The heater coil 38 may be formed from supported 12.5-micron thin stainless steel foil. In this case the time of the heater to heat up or cool down to a constant temperature will be typically from less than a second to a few seconds. By way of example, the sensor chamber 16 volume may be between 1 cc (cubic centimeter) and 10 cc, and the pump chamber 36 volume may be from 5 cc to 200 cc. The volumes of the sensor and pump chambers may vary with specific design applications of the gas detector.

A diffusion preventing pump passage 40 provides a fluid connection between the pump chamber 36 and sensor chamber 16. The pump passage 40 may be formed of a tubing material that is the same or similar to the passage 32. The dimensions of the pump passage 40 and passage 32 are preferably selected so that the rate of gas diffusion through the passage 32 and pump passage 40 is lower than the average pumping flow rate. As an example, a diffusion rate of hydrogen through a 1 mm inside diameter (ID) tube with 500 mm length at normal conditions will be close to 0.0001 $cm^3$/sec. This flow rate is sufficiently small when compared with the typical 0.1 $cm^3$/sec of the averaged rate of gas sampling into the sensor chamber by convection. The diffusion rates of gases other than $H_2$ are even lower. On practice, non-zero diffusion rate will introduce a measurement error so insignificant, that this is usually not a problem. Obviously, the diffusion can be further reduced or zeroed by employing a known mechanical shut-off devices such as e.g. solenoid valves.

Figure 2:
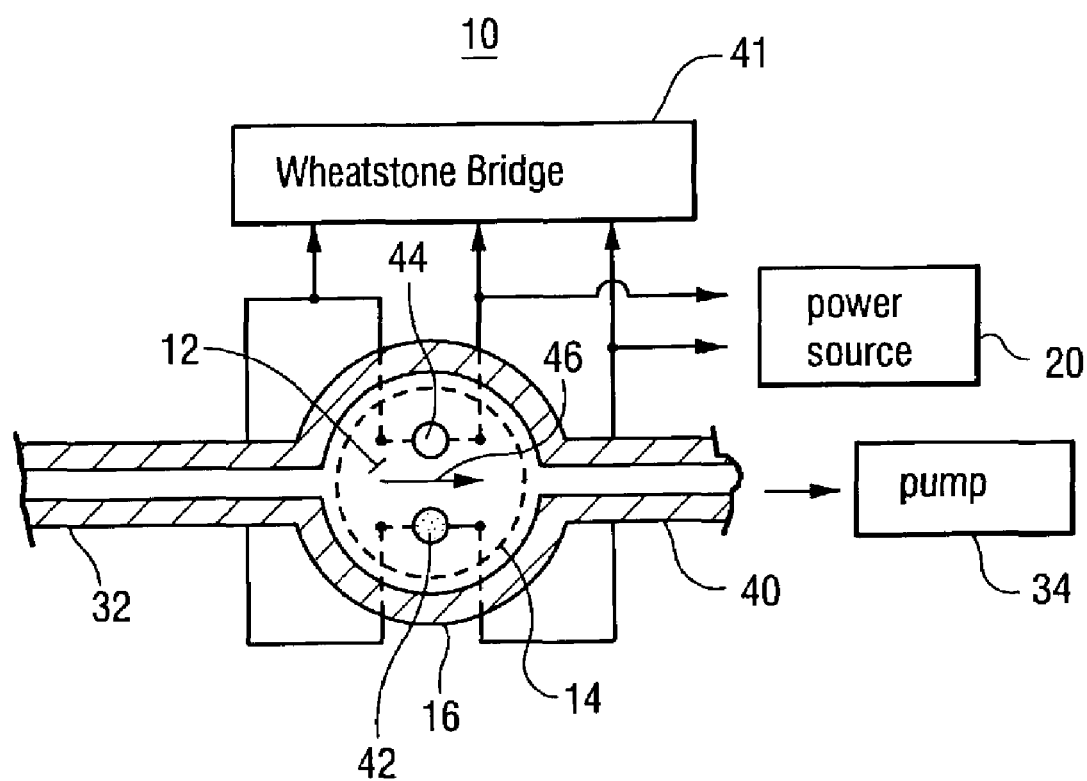
FIG. 2 is a schematic diagram showing in cross-section flow-through enclosure for a catalytic bead and reference bead of the combustible gas detector shown in FIG. 1.

FIG. 2 is a schematic diagram of a top-down, cross-sectional view of a part of the detector 10, including the sensor 12, enclosure 14 and chamber 16. The catalytic sensing bead 42 and reference bead 44 are preferably arranged symmetrically in the enclosure 14 and chamber 16. The beads 42 and 44 are arranged symmetrically with respect to the gas flow 46 passing through the enclosure 16. For example, the beads may be equidistant from each other on opposite sides of the axis of the flow path 46 through the chamber 16. The beads are aligned in the flow path such that both beads are exposed to substantially the same flow conditions at substantially the same time, while being spatially offset from each other in the sensor enclosure 14. Because the beads have similar gas exposure conditions, the response of the sensing bead and reference bead to gas flow should be the same, except for the burning of combustible gases on the sensing bead 42 only.

The symmetric alignment of the beads 42, 44 with respect to each other in the flow path 46 should minimize any "offset" sensor signal when there are no combustible gases in the sample gas flow. It was found by experiment that a balanced positioning of the beads minimizes the offset to the equivalent of less than 20 ppm of combustible gases in a gas sample at typical flow rates through the chamber 16 of up to several cubic centimeters per second. If the beads are not symmetrically arranged, the offset sensor signal may be significant. Such large offset sensor signals are common in conventional sensors because the catalytic sensing bead and reference bead are positioned in the flow path which tends to change direction and rate randomly. The RTDs of the beads will respond non-symmetrically, for example, when one bead is upstream of the other bead or the beads do not see substantially the same flow conditions of the gas sample.

Figure 3:
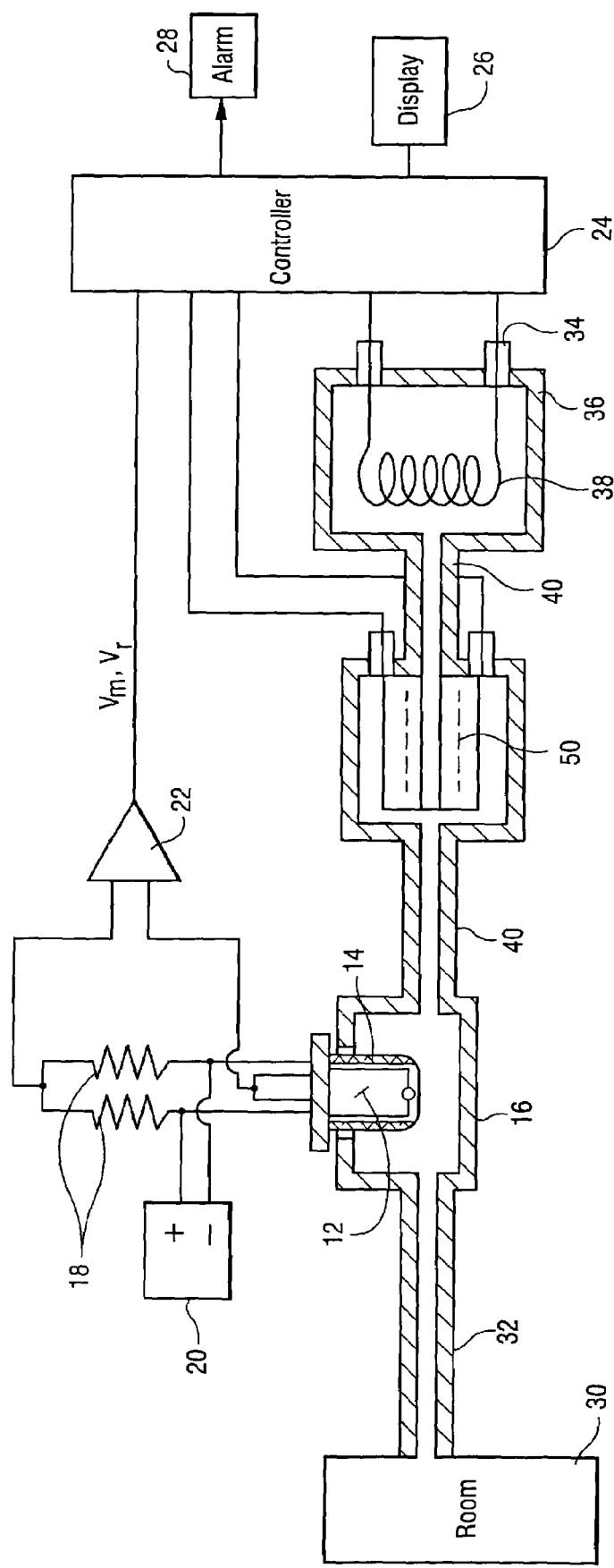
FIG. 3 is a schematic diagram showing in cross-section a second embodiment of a combustible gas detector.

As shown in FIG. 3, the detector 10 may also include a "blow-through" current-controlled electrolyzer 50 positioned in the pump passage 40. The electrolyzer is pneumatically connected between the sensor chamber 16 and the pump 34. The electrolyzer is designed for generating hydrogen gas (and oxygen) when electrical current passes through its matrix capable to absorb ambient moisture from the gas flowing through the pump passage 40. A suitable fast response electrolyzer is known and shown in USSR Patent No. 1170277.

The gas sample flow rate into the sensor chamber, while being relatively low at any time for not introducing flow error, exhibits rapid relative changes from zero to maximum, usually in a few seconds time. The gas sampling is interrupted for a periods of 5 to 30 seconds to zero the sensor. This timing is given as an example only and the invention is not limited to these periods. Accordingly, a gas mixture from outside is sampled into the sensor chamber 16 not constantly, but by relatively small portions. Combustible gas(es) in each sample portion is allowed to burn (and raise the temperature of the sensing bead), preferably until the burn-out of combustible gases in the sample is essentially completed, and only then the gas portion in the chamber 16 is replaced. Secondly, it should be noted, that gas flow in and out of the "breathing" pump 34 occurs only when the coil temperature changes. When the pump heating coil remains at a constant temperature (e.g. while heated constantly), the "breathing" stops and flow of the gas through the chamber 16 remains practically zero. In other words, intermittent and relatively short (e.g. 1-second) "inhale" and "exhale" are divided with a longer (e.g. 15-second) pause.

Figure 4:
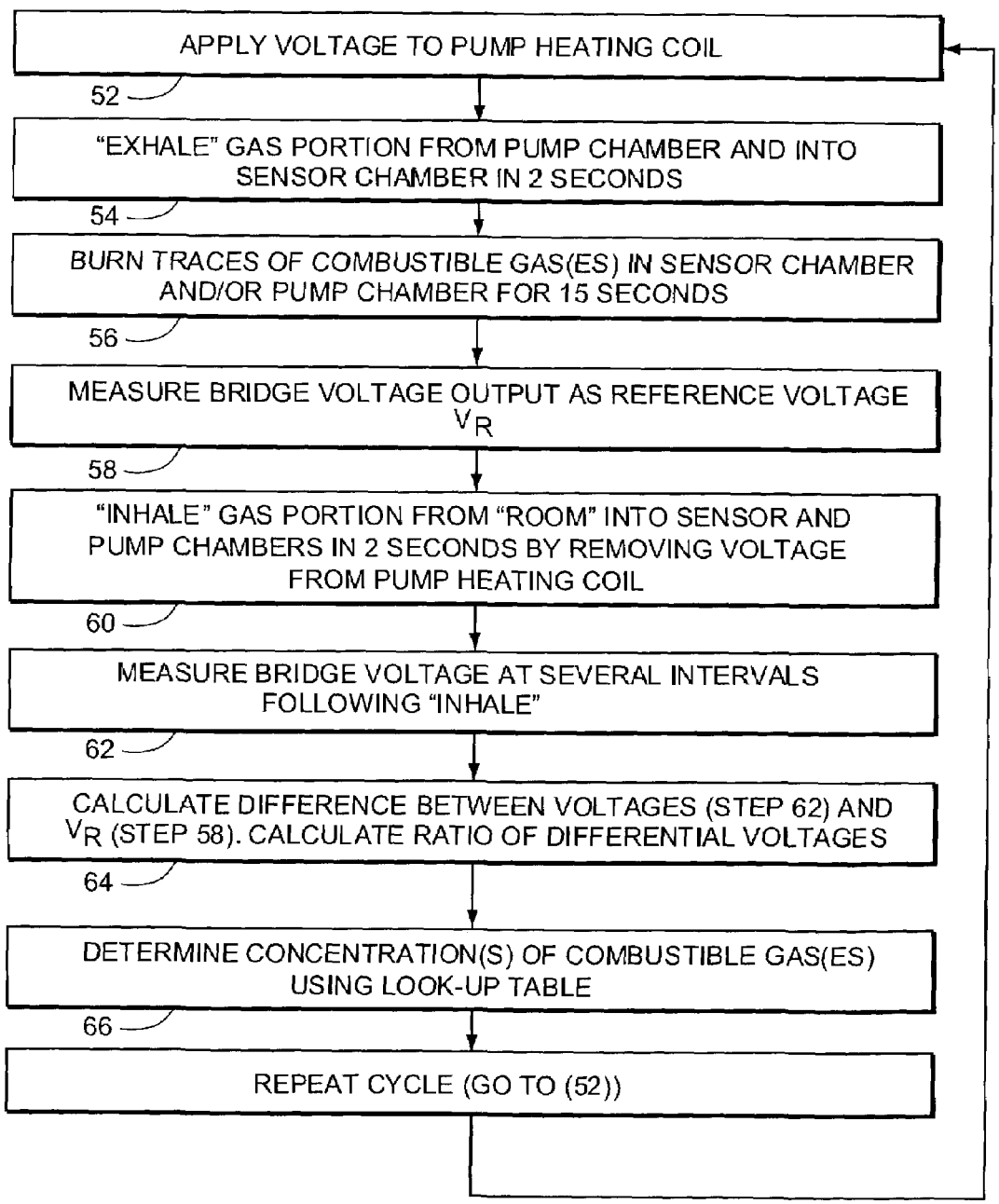
FIG. 4 to 6 are flow charts of a gas sampling and calibration processes.
Figure 5:
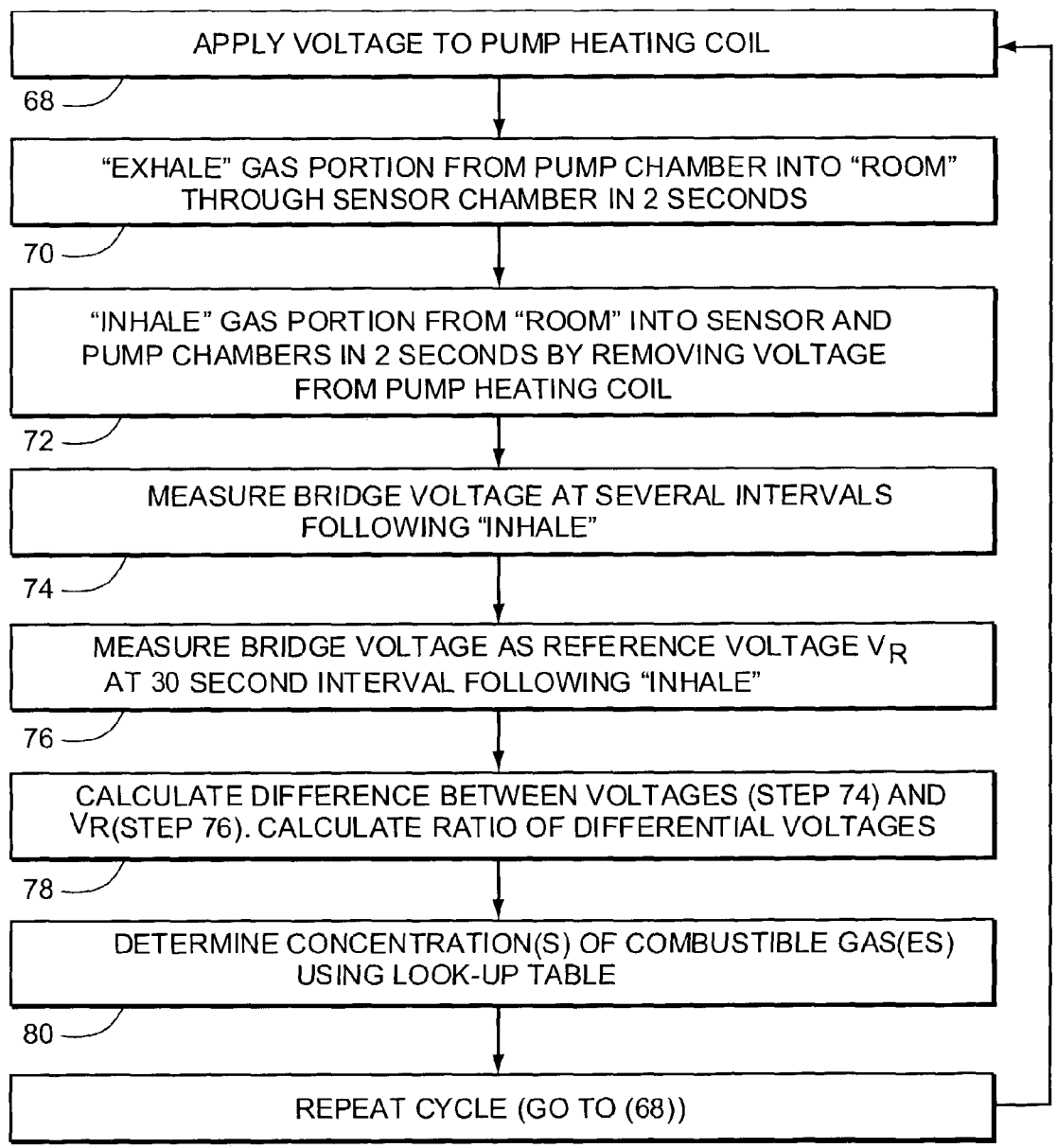
Figure 6:
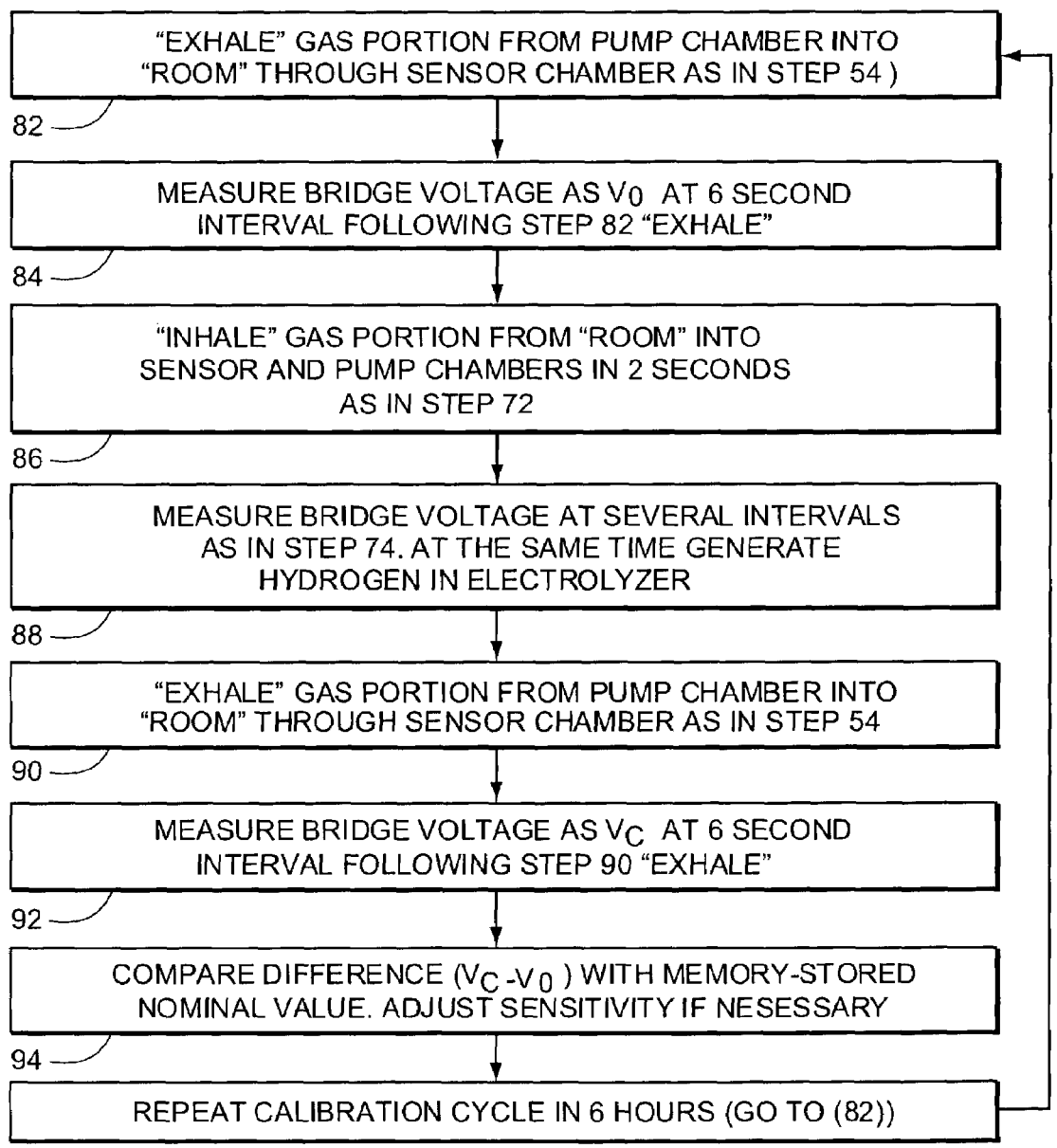

FIGS. 4 to 6 are a process chart of exemplary steps of operating the detector 10. FIGS. 4 and 5 show alternative combustible measurement cycles, each with automatic zeroing ($V_r$) steps. FIG. 6 shows a calibration process to check whether a detector is poisoned. The gas detector 10 may be electrically powered, e.g. by 3 Watts, to heat up the "breathing" pump heater coil 38 in step 52,68. The controller 24 may power the coil 38 for a fixed period of time. When powered, the temperature of the heater coil rises within a few seconds, to between 100° C. and 200° C. above ambient temperature, for example. While the coil heats the gas inside the pump chamber 36, the heated gas pushes itself out through the pump passage 40, sensor chamber 16, passage 32, and into the volume 30 to purge the detector 10, in step 54. During and especially after this purge period (when gas flow for some time remains virtually zero), combustible gases that may be present in the pump and/or passage 40 would flow into the sensor chamber 16 and burn out on the sensor catalyst bead 42 and/or on the heater 38, in step 56. The reference voltage measurement process may be performed just before sampling a gas (see FIG. 4) or after sampling (see FIG. 5).

A technique to expedite the burn out of combustible gases during the purge step, in the sensor chamber, is to burn gases in the pump chamber, in step 56. For example, a thin layer of Pt may be applied to the heater coil 38 to promote catalytic combustion. When the coil 38 is heated, combustible gases in the pump chamber 36 are substantially burned out before they can flow through the pump passage 40 and into the sensor chamber 16.

After the gas flow into the chamber 16 has been interrupted and the sensor 12 burns down combustible gases already in the sensor chamber 16, in step 56, the output of the Wheatstone bridge is measured, in step 58. The measurement is digitally stored in the controller memory for future use as the reference voltage $V_r$. "Reference voltage" ($V_r$) may be defined as the "zero combustibles" bridge voltage output after the gas flow into the chamber 16 has been interrupted and the combustibles in the chamber are essentially completely burned out. Alternatively, the reference voltage may be measured after the gas has initially been sample. The conditions suitable for the reference voltage $V_r$ to be accurately measured in this case are achieved in about 30 second or more time interval after the gas sample flow has been interrupted (end of the "inhale"), in step 76.

The controller 24 turns off the heater 38, and allows the thin-film heater coil 38 to cool, which typically takes for about one to three seconds. While the heater 38 and the gas in the pump chamber cool down, the pump inhales a portion of the sample gas from the room 30, in steps 60,72. The pump inhales a known and fixed (usually small) sample of gas from the room volume 30, through the diffusion-limiting passage 32 and into the sensor chamber 16.

Combustible gases in the inhaled gas sample burn on the catalyzed sensing bead 42, in steps 62, 74. Optionally, the gas sample is allowed to stay in the chamber 16 until the combustibles burn out virtually completely (usually for about 30 seconds). At this time, the sensor output is measured as the reference voltage $V_r$, in step 76.

During the pump "inhale", a gas sample is quickly drawn into the sensor chamber in a controlled amount. As the combustibles in the gas sample burn, the temperature of the sensing bead 42 temporarily rises and causes a change in the bead resistance. The temperature rise of the sensing bead causes the Wheatstone bridge to produce a bridge output voltage $V_m$ that is indicative of the sensing bead temperature. The bridge output voltage is measured at one or more gas sample measurement times, in step 62.

The controller detects the combustible gas concentration in the sampled gas by determining the difference between $V_r$ and $V_m$ for one or more sample measurement times, after the gas sample is "inhaled" by the pump, in steps 64, 78. This differential series of voltage measurements allows the controller to generate accurate and precise readings of the combustible gas(es) concentration in the sampled gas for a long period of time (i.e. for several years without manual calibration) by using a memory-stored look-up table, as in steps 66,80. The look-up table converts the differential voltage measurement to a combustion temperature of the sample gas.

The variations in the ambient background gas are compensated for by frequent zeroing of the sensor and, do not affect the differential sensor measurement of the combustible gas(es) concentration.

The catalytic sensor bead temperature will increase and then decrease as the "inhaled" sample with combustible gases burns and until it burns out virtually completely in the chamber 16. Based on experiments conducted of an embodiment of the detector 10, dynamic characteristic of the bridge output depends on the type of combustible gas and/or the ratio of two or more combustible gases concentrations simultaneously present in the sample. For instance, a maximum rate of burning and consequent maximum bridge output voltage will be achieved in about five seconds after the "inhale" of gas sample with hydrogen only as a combustible, and in about nine second with CO only. This data is based on a gas sample "inhale" time of less than two seconds. In $H_2$/CO gas mixtures, the maximum rate of burning (indicative by maximum bridge output voltage) gradually shifts during the five to nine second interval, with the relative increase of CO concentration vs. $H_2$ in the mixture. The rate of temperature increase in the sensor 12 due to a fast introduction of new gas sample into the chamber 16 is indicative of the composition of combustible gases mixture. The rate of temperature increase of the sensing bead can be determined, e.g., by measuring the Wheatstone bridge output at several time intervals following the "inhale" period. The rate at which the combustible gases burn depends on the diffusion coefficient of the specific combustible gas in the sample and on the catalyst temperature. Otherwise, the amplitude of the temperature increase of the sensing bead 42 is proportional to the concentration of combustible gas(es) in a range from the lower sensor detection limit to several percent of combustible gas concentration.

In general, a change in amplitude and rate of heating of the sensing bead due to different compositions of the combustible gases can be analyzed by having the controller 24 identify the type and concentration(s) of combustible gas (es,) or evaluate the ratio between two combustible gases in a gas sample drawn into the sensor enclosure 16 from the room volume 30.

It was found experimentally, that a simplified algorithm might be used to determine the ratio between $H_2$ and CO concentrations as well as the concentration of the sum of these gases with practically sufficient accuracy. For this purpose, three Wheatstone bridge outputs $V_5$, $V_{12}$, and $V_r$ are measured at three different time intervals, respectively, following the gas sample "inhale". The time intervals (delays) between the start of "inhale" (which duration is about one second) and voltage measurements are 5 seconds, 12 seconds, and 30 seconds for $V_5$, $V_{12}$, and $V_r$, respectively. The difference $V_{12}-V_r$ was found to represent the sum of CO and H2 concentrations (independently from their ratio in the sample gas) and can be used to determine the concentration of CO and $H_2$ combustibles by having the controller 24 use a look-up table. The ratio $(V_5-V_r)/(V_{12}-V_r)$ is generally in a range of 0.9 to 1.7 and practically linearly depends on the CO/H2 ratio, with the ratio of 0.9 corresponding to 100% CO and the ratio 1.7 corresponding to 100% $H_2$. The timing and/or $(V_5-V_r)/(V_{12}-V_r)$ ratio equivalent may be specific to a specific sensor type and sensor chamber geometry. Generally, it may require a preliminary calibration. By determining $(V_5-V_r)/(V_{12}-V_r)$, the concentrations of CO and $H_2$ can be determined for each gas. Thus, the individual and combined concentration levels of CO and $H_2$ can be determined from a single measurement cycle and at the same temperature of the sensor beads. The differential voltages $(V_5-V_r)$ and $(V_{12}-V_r)$ are measured in step 64. In step 66, the total concentration of CO and $H_2$ (individually and in sum) may be found by the controller using comparing the CO to $H_2$ ratio look-up table, and performing a linear approximation.

To determine the concentrations of CO and $H_2$ separately and with relatively high accuracy, a measurement cycle of one minute or longer may be required. Significantly shorter measurement cycle may be used if the composition of the gas sample with respect to combustible gas(es) is known and the sum of combustible gases is the only interest. Alternatively, shorter and longer measurement cycles can be alternated with a software initiated switch in the controller. For example, by using a "long" measurement cycle the controller can initially measure CO/H2 ratio once in a given process. The controller may subsequently automatically apply a "fast" measurement cycle(s) that assumes that the measured CO/$H_2$ ratio is a constant known quantity (as measured at the last long cycle). Periodically, the controller may perform a long cycle to re-measure CO/$H_2$ ratio.

With relatively short time intervals between gas samplings ("inhales") the combined concentration of combustibles can be determined by measuring the difference between maximal and minimal values of the sensor output within measurement cycle, which is in practice the alternating part of a full sensor signal.

The detector automatically performs a "zero" auto-calibration after each measurement cycle, in step 66. The auto-zeroing method enables the detector to accurately measure small amounts of combustibles in a sample gas by detecting changes in the temperature of the sensing bead within measurement cycle down to about 0.002° C. Auto zeroing may be performed by measuring the reference sensor output ($V_r$) either at the end of the "inhale" step, as in step 76, or just before the end of the "exhale" step, step 58.

During the measurement cycle the detector may "inhale" a small gas sample, e.g., 0.1 cc to 1 cc, into the sensor chamber 16. As the chamber may have a volume of about 2 cc, the small gas sample becomes diluted (when entering the chamber having a chamber volume substantially larger than the gas sample). In our experiments, the detector reliably measured "external" $H_2$ concentration up to 8% of hydrogen (2 LEL) in air.

Auto-calibration of sensitivity may be performed periodically, e.g., once every several minutes to once every several hours. When an ambient moisture type electrolyzer is used, a re-calibration cycle time is limited by replenishing the electrolyzed water back from sample gas. Typically, the 5 $mm^3$ to 10 $mm^3$ of $H_2$, needed for a single calibration is replenished by ambient moisture ideally in about 20 minutes even at a −30° C. Dew (Frost) Point (DP) condition. The higher the DP, the faster the replenishment by ambient moisture. In reality, it may take more than an hour to replenish, especially for a low DP gas sample. The moisture limitation is not an issue with regards to flue gas analysis, because DP temperature of flue gases is usually close to +50° C. It should be noted, that presence of hydrogen or hydrocarbons in air even well below LEL would generate significant amount of moisture due to combustion on the sensor.

As shown in FIG. 6, sensitivity calibration starts at a regular (first) pump "exhale" of residual gas portion through the chamber 16 and further outside into the room, as in step 82. The sensor output ($V_0$) is measured with a pre-determined time delay after the start of "exhale" (Step 84). After the regular "inhale" (step 86) but before the beginning of the next (second) "exhale" step, a pre-determined amount of electricity passes through the electrolyzer 50 to generate a fixed amount of hydrogen inside the enclosure 51 of the electrolyzer, in step 88. For this purpose the electrolyzer is powered by a fixed current, e.g. in the range from 1 mA to 10 mA, and over a fixed period of time, e.g. from 1 to 10 seconds. This period for generating hydrogen should be preferably less than period between the pump "exhale" and "inhale" steps during regular sample gas measurements. A relatively small amount of hydrogen generated, e.g. from 0.1 $mm^3$ to 10 $mm^3$, is usually sufficient for the calibration.

The pump "exhales" for the second time in step 90. The gas portion carried over from the pump through the electrolyzer chamber 51 and into the chamber 16 during the second "exhale" contains a fixed amount of hydrogen generated in the electrolyzer. The sensor output ($V_c$) is measured, in step 92, during the burning of hydrogen and preferably with the same time delay from the start of the second "exhale", as $V_o$ after the start of the first "exhale". This delay time is usually in the range of 2 seconds to 10 seconds with the most optimal value corresponding to the time of maximum combustion rate of hydrogen introduced as a sample into the sensor chamber, typically close to 6 seconds. Due to the controlled (fixed) amount of the gas "exhaled" and the repeatable amount of hydrogen generated, the calibration process can be repeated, e.g. every few hours, with sufficiently high accuracy and repeatability within the extended period of time, e.g. for several years. The electrolyzer may not require manual service for years, as the electrolyzed water is replenished from the environment.

The difference between $V_c$ and $V_0$ is evaluated by the controller 24 and compared with a memory-stored acceptable range for this difference, in step 94. If the sensor is sufficiently sensitive, then the difference between $V_c$ and $V_0$ will be within the predetermined range. Based on the $V_c$-$V_o$ comparison, in step 94, a decision or automatic action concerning the sensitivity of the sensor and sensor adjustment is made. $V_0$ and $V_c$ may be measured ether as differential signals with respect to $V_r$, or as absolute values. Anyway, $V_r$ is cancelled out during the subtraction of $V_0$ from $V_c$.

With the zero sensing method shown in FIG. 6, sensor poisoning may be quickly detected by automatic calibration after each calibration cycle. As sensitivity calibration is performed during the "exhale" phase of the measurement cycle, the calibration is virtually transparent to the detector user, and does not interfere with or interrupt the regular LEL measurements. Relatively small amount of oxygen generated in parallel with hydrogen does not affect the sensor calibration accuracy, as a significantly larger amount of $O_2$ usually is already present in the gas sample.

The detector 10 disclosed herein may include features and functions such as: a transparent automatic "zeroing" between each measurement to improve long-term stability and minimize calibration requirements; reduced exposure of the sensing beads to gas samples that may contain sensor poisoning components; measurements of CO and $H_2$ concentrations separately, which may have particular application in flue gas analysis; measurements of the concentration of combustible gases at levels of detectivity down to ±10-ppm (parts per million); measurement of combustibles in high ambient gas flow rate applications such as inside a gas turbine enclosure; a sensor can be remotely located, up to several meters, from a sampling point; automatically monitoring and adjustment of sensor sensitivity while the sensor is on-line; reliable measurements of the concentration of combustibles significantly above LEL levels with fast sensor recovery for subsequent measurements.

Zero and sensitivity calibrations, as described herein, may both be employed as auxiliary and relatively infrequent (e.g. once in several hours) procedures in a sensor with otherwise uninterrupted gas sampling and a known standard bridge output measurement to fulfill the requirements of LEL detector fast speed of response.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to measure combustible gases using a catalytic sensor comprising:
   housing the catalytic sensor in a flow-through chamber to minimize gas diffusion to the sensor from a volume of ambient gas;
   drawing a gas sample of the ambient gas into the chamber from the volume;
   measuring a first output of the catalytic sensor as the ambient gas flows into the chamber;
   interrupting the flow of the ambient gas into the chamber;
   measuring a second output of the catalytic sensor during the flow interruption, and
   determining a condition of the combustible gases based on the first output and the second output.

2. The method as in claim 1 wherein the flow of ambient gas is drawn into the chamber by convection.

3. The method as in claim 1, wherein said interruption of the gas flow is maintained during catalytic combustion of the gas sample in the chamber.

4. The method as in claim 1 wherein the steps of the drawing the gas sample, measuring the first output, interrupting the flow and measuring the second output are a measurement cycle, which cycle is repeated periodically.

5. The method as in claim 1, further comprising: analyzing multiple sensor output measurements to determine the condition as a concentration of at least one combustible gas of a plurality of combustible gases in the gas sample.

6. The method as in claim 1, wherein determining the condition comprises determining a concentration level of at least two combustible gases in the gas sample based on multiple sensor output measurements.

7. The method of claim 1 further comprising powering the sensor prior to the first output measurement and until after the second output measurement.

8. The method of claim 1 wherein the sensor is continually powered from prior to the first output measurement and until after the second output measurement.

9. The method of claim 1 wherein the measurement of the first output is performed synchronously with the drawing of the gas sample.

10. The method of claim 1 wherein the measurement of the second output is made after combustible gases in the chamber have been consumed.

11. The method of claim 1 wherein the second output is indicative of no combustible gases in the chamber.

12. The method of claim 1 wherein the interruption of flow and measurement of the second output follows drawing the gas sample and measuring the first output.

13. A method to measure combustible gases using a catalytic sensor comprising:
    housing the catalytic sensor in a flow-through chamber to minimize gas diffusion to the sensor from a volume of ambient gas;
    drawing a discrete gas sample of the ambient gas into the chamber from the volume;
    interrupting a flow of the ambient gas into the chamber after the gas sample has flowed into the chamber, and measuring an output of the catalytic sensor synchronously with said interruption of the gas flow,
    wherein the steps of the drawing the gas sample, interrupting the flow and measuring the output are a measurement cycle, which cycle is repeated periodically and
    further comprising determining a concentration level of the combustible gases in the sample based on an amplitude of the variation in the sensor signal output alternating on the gas sampling frequency.

14. A method to measure combustible gases using a catalytic sensor comprising:
    housing the catalytic sensor in a flow-through chamber to minimize gas diffusion to the sensor from a volume of ambient gas;
    drawing a discrete gas sample of the ambient gas into the chamber from the volume;
    interrupting a flow of the ambient gas into the chamber after the gas sample has flowed into the chamber, and
    measuring an output of the catalytic sensor synchronously with said interruption of the gas flow,
    wherein prior to drawing the flow into the chamber, the method further comprises:
    purging the chamber of ambient gas;
    burning residual combustible gases in the chamber, and
    measuring a reference output signal from the catalytic sensor after burning the residual combustible gases in the chamber.

15. The method of claim 8 further comprising: determining a concentration of the combustible gas in the gas sample based on a difference between the sensor output signal and the reference output signal.

16. A method to measure combustible gases using a catalytic sensor comprising:
    housing the catalytic sensor in a flow-through chamber to minimize gas diffusion to the sensor from a volume of ambient gas;
    drawing a gas sample of the ambient gas into the chamber from the volume;
    measuring a first output of the catalytic sensor as the ambient gas flows into the chamber;
    interrupting the flow of the ambient gas into the chamber;
    measuring a second output of the catalytic sensor during the flow interruption, and
    determining a condition of the combustible gases based on the first output and the second output,
    wherein the interruption of flow and measurement of the second output precedes drawing the gas sample and measuring the first output.

* * * * *

UNITED STATES PATENT AND TRADEMARK OFFICE
CERTIFICATE OF CORRECTION

PATENT NO. : 7,062,952 B2　　　　　　　　　　　　　　　　　　　　　　　Page 1 of 1
APPLICATION NO. : 10/442070
DATED : June 20, 2006
INVENTOR(S) : Gokhfeld It is certified that error appears in the above-identified patent and that said Letters Patent is hereby corrected as shown below:

In claim 15 (column 12 line 33) the phrase "...claim 8" should read "...claim 14"

Signed and Sealed this

Third Day of October, 2006

JON W. DUDAS
*Director of the United States Patent and Trademark Office*